(12) United States Patent
Johnson (10) Patent No.: US 7,475,487 B1
(45) Date of Patent: Jan. 13, 2009

(54) HEIGHT RECORDING ALBUM

(75) Inventor: Dennis E. Johnson, Oostburg, WI (US)

(73) Assignee: Parchmint, Inc., Mequon, WI (US)

( * ) Notice: Subject to any disclaimer, the term of this patent is extended or adjusted under 35 U.S.C. 154(b) by 0 days.

(21) Appl. No.: 12/031,040

(22) Filed: Feb. 14, 2008

(51) Int. Cl.
- *G01B 5/00* (2006.01)
- *A61B 5/103* (2006.01)
- *A63H 33/08* (2006.01)

(52) U.S. Cl. .................... 33/512; 33/493; 33/832
(58) Field of Classification Search ............ 33/512, 33/832–833, 492–494, 483–484, 11–12; 40/219, 360, 626, 628, 630, 900; D10/70–71; D6/303–307; 434/96, 187; 446/85, 108, 446/124, 125
See application file for complete search history.

(56) References Cited

U.S. PATENT DOCUMENTS

| | | | |
|---|---|---|---|
| 1,608,771 A | 11/1926 | Cary | |
| 1,974,085 A | * 9/1934 | Shields et al. | ................. 33/512 |
| 3,313,030 A | 4/1967 | Heys | |
| 3,336,674 A | 8/1967 | Higgins et al. | |
| 4,118,868 A | 10/1978 | Johnson | |
| D279,358 S | * 6/1985 | Lichtman | ...................... D10/71 |
| D390,871 S | * 2/1998 | Whitney | ...................... D19/26 |
| 5,996,240 A | * 12/1999 | Casper | ........................ 33/759 |
| 6,003,235 A | 12/1999 | Chen | |
| 6,079,780 A | 6/2000 | Bapst | |
| 6,129,386 A | * 10/2000 | Brata | ........................... 281/5 |
| 6,226,881 B1 | 5/2001 | Landauer | |
| D460,366 S | 7/2002 | Winter | |
| 6,519,868 B1 | 2/2003 | Pryor et al. | |

* cited by examiner

*Primary Examiner*—Yaritza Guadalupe-McCall
(74) *Attorney, Agent, or Firm*—Reinhart Boerner Van Deuren s.c.

(57) ABSTRACT

A height recording album for measuring growth and development of a subject is provided. The height recording album includes a cover, a plurality of interconnected journal pages and a mounting mechanism to secure the album to an interior door. The album includes measuring indicia for accurately aligning the top edge of the door with the corresponding correct height of the door before securing the album in place. Each journal page includes at least one transparent pocket configured to receive an insert card providing pre-printed calibrated measuring indicia and space for marking the subject's height and documenting information about the subject. The journal pages of the height recording album are fan folded and secured in the cover when the album is stored.

21 Claims, 9 Drawing Sheets

HEIGHT RECORDING ALBUM

BACKGROUND OF THE INVENTION

Field of the Invention

The present invention relates generally to a height recording album, and more specifically to an apparatus for documenting a child's progress and growth and for retaining photographs and/or other keepsakes therein.

With the ease of availability of digital photography, scrapbook and album making has become an increasing popular hobby for retaining and preserving memories. These types of albums can be decorated, and/or can include letters, cards, keepsakes, newspaper clippings, and other mementos, in addition to photographs and personal journal inscriptions. Further, the advent of digital photography and desktop publishing has also facilitated the availability of customized, carefully selected photographs and drawings for inclusion into a project. The craft industry has developed specialized supplies such as books, papers, fabrics, pens, inks, and adhesives for the assembly of such a keepsake album.

Parents and grandparents are particularly interested in documenting and preserving a child's growth, progress and achievements over their lifetime. Baby books, photo boxes, journals and calendars are all great ways of keeping these memories together, but they can lack organization and can be difficult to chronologically correlate the child's achievements with their actual physical attributes at the time of the achievement.

Growth charts and child measuring devices are available, however, many lack the ability to simultaneously journal special events or record progress in the subject's life. These types of standard measuring charts also lack the ability to store coordinating photos, awards and other preserveable memories along with the child's physical milestones and development. Accordingly, new and creative ways to measure and record the growth and developmental progress of children, while also providing an attractive and compact album for preserving and displaying such information are needed.

SUMMARY OF THE INVENTION

With this invention, a height recording album is provided for documenting a child's growth from year to year, in a protected, compact and attractive album form. The height recording album of the present invention provides an organized space along side the child's height measurement that is intended to receive photographs, journal entries and/or milestones about the child.

A first embodiment of the height recording album includes a protective cover, a plurality of interconnected journal pages containing removable insert cards for documenting the child's growth and an integral mounting mechanism. The height recording album can also include an integral closure for securing the cover when the album is being stored. The height recording album additionally includes a marking device used to measure and mark the child's height on the album and a display stand.

The cover is designed to protect the journal entries and height measurements within the height recording album for an extended period of time. The cover is preferably constructed of a single piece of material and formed to provide a front cover, spine and rear cover for the album. The front cover includes an opening that will be used both as a viewing window for the contents of the album, and also for mounting the album to the top edge of a door, as described below.

The cover is constructed of a stiff or substantially rigid material, including, but not limited to, thermoplastic or polymer materials such as polypropylene, polyethylene, polystyrene, silicones, polyurethanes, acrylics or combinations thereof. The cover can be alternatively or additionally constructed of materials including, but not limited to, laminated or coated papers, cardboard, recycled fibers or other cellulose based or composite materials. The color and size of the cover is a matter of design choice and/or depends on the particular application for the album. For example, the cover can be colored or include indicia thereon that reflects the child's interests.

The height recording album includes a plurality of interconnected journal pages having hinge or fold lines formed in between each of the journal pages so that the journal pages can be pivoted/folded with respect to each other, and folded into an accordion-pleated or fan folded stack. The top two journal pages are aligned with and permanently joined to the inside surface of the cover with an adhesive or by other permanent means known to those skilled in the art. As such, the top journal page will include an aperture that aligns with the opening in the front cover. The top journal page also includes calibrated graduations adjacent to the aperture that correspond to the height of a conventional interior door including heights ranging from about 78 inches to about 85 inches from the floor to the door's top edge, although a smaller or larger range may be used, as a matter of design choice.

Each of the journal pages is formed from a backing sheet and a plurality of transparent pockets. A first set of pockets is design to fit photographs of the child to correspond to the particular age of the child at the time of height measurement. A second set of pockets, adjacent to the first set of pockets, is designed to accommodate the insert cards for marking the child's height. Alternatively, there can be a single larger pocket, adjacent to the first set of pockets, that will include a single, larger insert card.

The backing sheet is preferably opaque or the same color as the cover; however, consistent with the broader aspects of the present invention and as a matter of design choice, the backing can be semi-transparent or transparent. The backing material and the pockets of the journal page are each preferably constructed of substantially lightweight yet durable material including, but not limited to, thermoplastic or polymer materials such as polypropylene, polyethylene, polyester, polystyrene, silicones, polyurethanes, acrylics or combinations/composites thereof. The backing material and pockets can be alternatively or additionally constructed of materials including, but not limited to, laminated or coated papers, cardboard, recycled fibers or other cellulose based or composite materials, provided the pockets themselves are formed of a transparent material. It will be appreciated that the backing and the pockets can be constructed of different types or combinations of materials.

The height recording album of the present invention further includes a plurality of insert cards configured to fit within the second set of pockets on each journal page. Each insert card includes a portion that extends outside the pocket including printed measuring indicia and space for marking the height of the child or subject. The printed measuring indicia is calibrated and is preferably provided in both English and metric units. When the height recording album is assembled, the pockets of each journal page will contain an insert card. When the journal pages are unfolded from the stack, the calibrated measuring indicia of the insert cards are arranged in numerical order, providing the height album with an accurate, graduated measuring scale.

The height recording album also includes an integral mounting mechanism used to mount the album to a door when height measurements are taken. The mounting mechanism includes a string or cord having first ends that are secured to the inside surface of the cover. A second end of the cord includes an adjustable loop sized to fit over and tighten around a door knob of the door. The integral mounting mechanism can be easily stored within the cover when the height recording album is displayed.

To use the height recording album of the present invention, the cover is opened and the fan folded stack of journal pages is unfolded so that they may be fully extended. The cord of the mounting mechanism is unwound from its stored position and threaded through the opening in the front cover. The cord is slipped over the top edge of the door and the looped end fits over the door knob.

The height of the door from the floor to the top edge of the door is then measured. Using the measuring indicia adjacent to the aperture on the top journal page, the top edge of the door is then aligned with the appropriate calibrated graduation for the correct height of the door. A clasp or retainer is used to tighten the end of the cord around the door knob, fixing the height recording album at the correct vertical position. Once secured, the calibrated measuring indicia on the insert cards of the height recording album provides an accurate scale for measuring a child's height.

The marking device is then used to measure the child's height and it is marked on the journal page. Once the height measurement is taken, the insert card within the transparent pocket on the journal page can be removed to include information about the child's progress, likes and dislikes, school, etc. on the front and/or back surface thereof. In addition, a photograph, cut to the correct size, can be placed into the transparent pocket next to the marked height measurement—reflecting the child at the age the height is measured.

After the height measurement and journal entry are made, the album is removed from the door by loosening the cord around the door knob, removing the height recording album from its fixed position and storing the mounting. The journal pages are again folded into the fan folded stack and placed within the cover protecting the album's contents. If the album is provided with an integral closure, it is then fastened and the album can be placed in a display stand or stored on a shelf.

Another embodiment of a height recording album includes an alternate, external mounting mechanism and combination display stand. The mounting mechanism is provided separately from the height album and includes a back plate and a hanger bracket secured together with a fastening mechanism. The back plate includes a vertical slot at approximately the center thereof and measuring indicia corresponding to the height of a conventional interior door vertically printed adjacent to the slot. The back plate also includes laterally spaced apertures sized to accommodate hangers such as pegs, pins or the like to hang the album.

The hanger bracket is a substantially U-shaped member having a flat bottom portion and laterally spaced legs. Vertical fold lines allow each of the legs to pivot so that the hanger bracket can be used to mount the album to the top edge of the door. A guide extends perpendicularly from the hanger bracket, which is sized to fit through and slide back and forth within the slot of the back plate.

To use the external mounting mechanism, the hanger bracket is positioned in its inverted position (upside down U position) with its legs pivoted substantially ninety degrees away from the bottom portion thereof, providing the hanger bracket with a hook-like feature. The bracket is moved so that its bottom edge is aligned with the appropriate calibrated graduation for the correct height of the door. The fastening mechanism is then positioned to secure the bracket into place on the back plate. The mounting mechanism is then positioned so that the hanger bracket rests on the top edge of the door.

In this position, the hangers/pegs of the back plate project forward to a distance sufficient to permit the album to be hung therefrom. As such, the album is then mounted to the top edge of the door by hanging it on the back plate tabs using the opening in the front cover. Once secured, the calibrated measuring indicia on the insert cards of the height provides an accurate scale for measuring a child's height. After the height measurement and journal entry are made, the album is pulled away from the pegs of the mounting mechanism. The journal pages are again folded into the fan folded stack with the cover protecting the album's contents.

The mounting mechanism is then converted into a display stand by loosening the fastening mechanism and positioning the bracket into an upright position (U position) and then retightening the fastening mechanism. The legs of the bracket are pivoted substantially ninety degrees away from the back plate. The edges of the back plate can be folded backwards, away from the legs of the bracket to provide support to the display stand. The album can then be displayed in the stand.

The apparatus of the present invention is of a construction which is both durable and long lasting, and which will require little or no maintenance to be provided by the user throughout its operating lifetime. The apparatus of the present invention is also of inexpensive construction to enhance its market appeal and to thereby afford it the broadest possible market. Finally, all of the aforesaid advantages and objectives are achieved without incurring any substantial relative disadvantage.

DESCRIPTION OF THE DRAWINGS

These and other advantages of the present invention are best understood with reference to the drawings, in which.

DETAILED DESCRIPTION OF THE PREFERRED EMBODIMENT

A first embodiment of a height album 50 of the present invention is provided in FIGS. 1 through 14. Another embodiment of a height album 300 consistent with the teachings of the present invention is illustrated in FIGS. 15 through 29. It will be appreciated that the features described with respect to one embodiment of the present invention may be included and/or substituted into the other described embodiment of the present invention.

Turning first to FIGS. 1 through 5, the height album 50 comprises, in its simplest form, a cover 52, a plurality of interconnected journal pages, indicated generally at 114, 136, 160, 162, 164, 166 and 168, respectively, for retaining a plurality of insert cards 74 and an integrally provided mounting mechanism, indicated generally at 68. The height album 50 additionally includes a measuring and marking device 72 and a display stand 76. A closure 70 may also be included, as described in more detail below.

The cover 52 preferably includes three portions, a front cover 78, a spine 80 and a rear cover 82. Each of the front cover 78, the spine 80 and the rear cover 82 have inside and outside surfaces, 84 and 86, 88 and 90, 92 and 94, respectively. The front cover 78 includes an opening 96 so that a photograph or other ornamentation can be seen therethrough when the album 50 is displayed. In addition, the opening an also be used to mount the album 50 to a door 500 when measuring the child's height, as will be described in more detail below. The cover portions are preferably constructed of a single piece of material, interconnected and separated from each other by hinge or fold lines 98. Fold lines 98 are formed into the material by conventional methods, such as crimping, depending on the type of material selected for the cover 52, as will be well known to those skilled in the art. The size of each of the front cover 78, spine 80 and rear cover 82 is a matter of design choice, provided that the interconnected journal pages 114, 136, 160, 162, 164, 166 and 168 can be neatly folded and retained therein. Preferably, each of the front cover 78 and rear cover 82 are about 8.5 inches by about 9.75 inches in size. In certain other embodiments, the front cover and rear cover can be a standard sheet size, like 8.5 inches by 11 inches. It will be appreciated that the thickness of the spine 80 will depend on the folded thickness of the interconnected journal pages and will be sized accordingly.

The cover 52 is preferably constructed of a stiff or substantially rigid material, selected to protect the contents of the album of a number of years. In certain preferred embodiments, the material can include, but not limited to, thermoplastic or polymer materials such as polypropylene, polyethylene, polystyrene, silicones, polyurethanes, acrylics or combinations thereof. The cover 52 can be alternatively or additionally constructed of materials including, but not limited to, laminated or coated papers, cardboard, recycled fibers or other cellulose based or composite materials. The thickness of the materials used for the cover 52 will depend on the material selected for construction. For example, as will be well known to those skilled in the art, thermoplastics will exhibit the required stiffness and durability required of the cover 52 at varying thickness.

It will be appreciated that the front cover 78, spine 80 and rear cover 82 can be constructed of three separate pieces of material and permanently joined together at the hinge or fold lines 98. Accordingly, the cover 52 can be constructed of different types or combinations of materials.

Figures 4, 5:
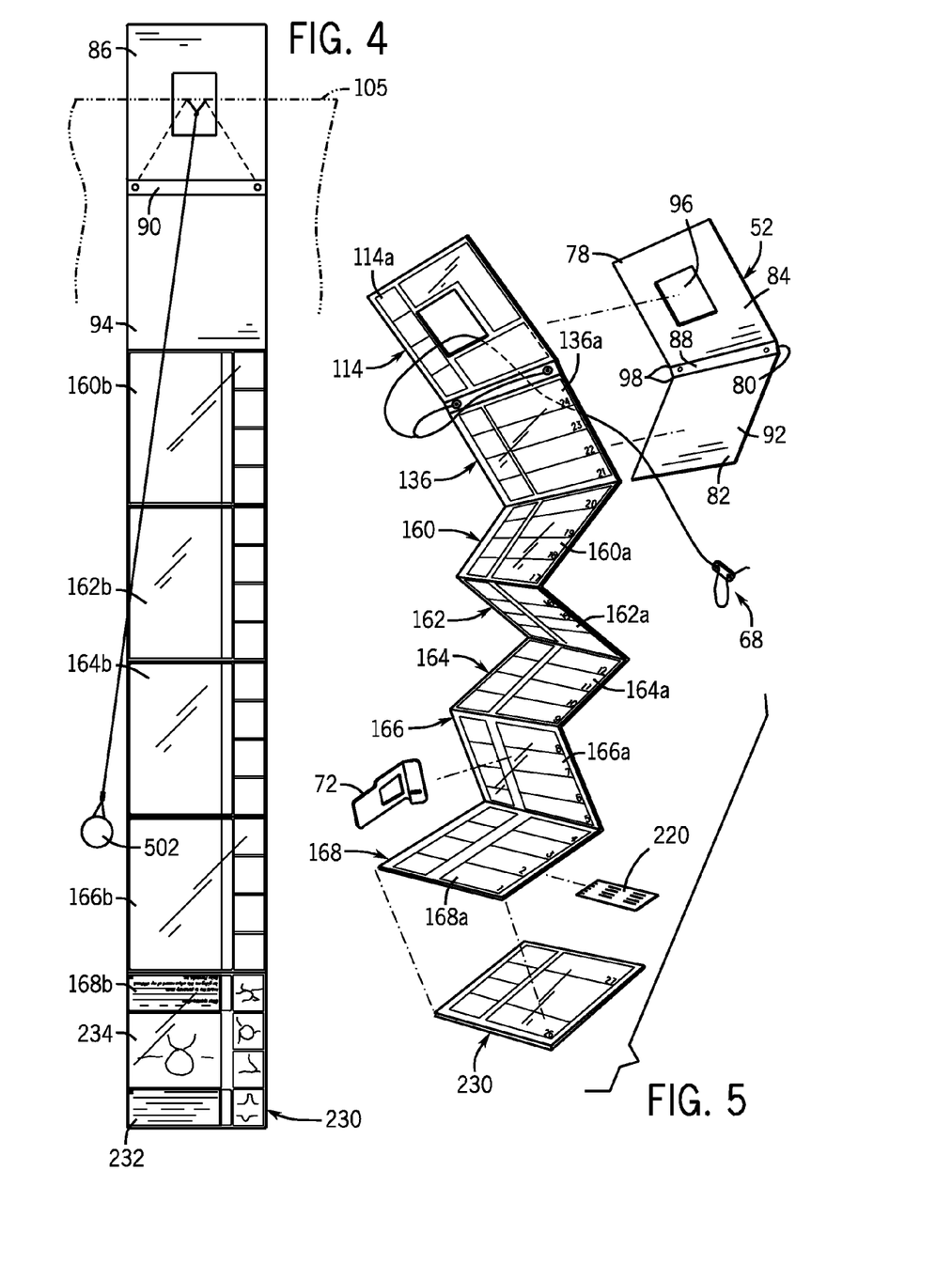
FIG. 4 is a rear plan view of the height recording album illustrated in FIGS. 1 through 3.
FIG. 5 is an exploded view of the height recording album illustrated in FIGS. 1 through 4.

Each of the journal pages 114, 136, 160, 162, 164, 166 and 168, are preferably connected to each other and have front and rear surfaces, indicated by (a) for front surface and (b) for rear surface, as shown in FIGS. 4 and 5. The first (or top) journal page 114 is substantially the same size as, or slightly smaller than the front cover 78 so that it can be aligned with and adhered to the inside surface 84 thereof.

Figure 7A:
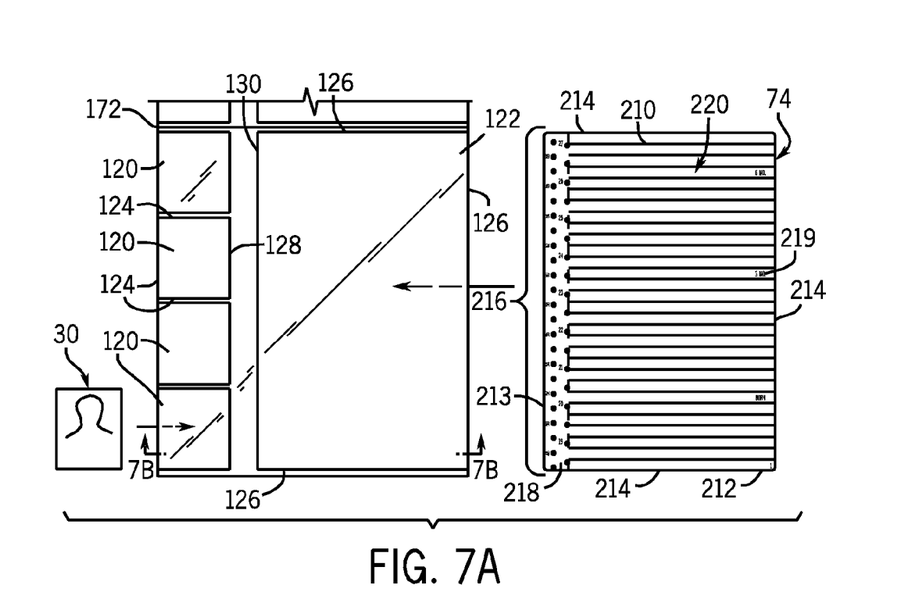
FIG. 7A is a first embodiment of a journal page and insert card used in the height recording album of the present invention.
Figure 7B:
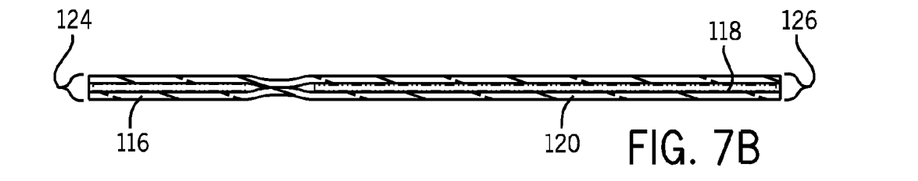
FIG. 7B is a sectional view of the journal page illustrated in FIG. 7A, taken along the line 7B-7B therein.
Figure 8:
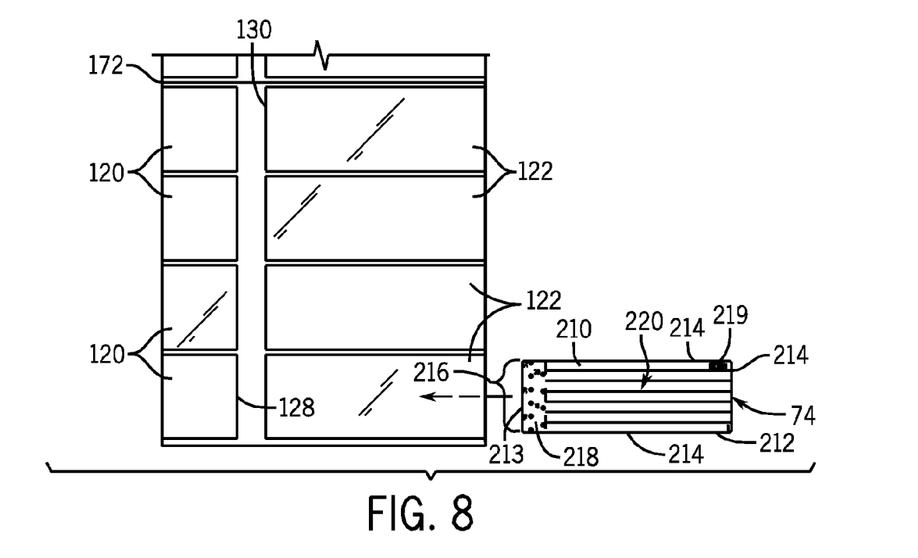
FIG. 8 is another embodiment of a journal page and insert card used in the height recording album of the present invention.

As best illustrated in FIGS. 7A, 7B and 8, each of the journal pages 114, 136, 160, 162, 164, 166 and 168 comprises a backing 116 having a front surface 118 and a back surface 120, and a plurality of transparent pockets 120 and 122 are formed on the front surface 118 of the backing 116. The backing 116 is preferably opaque or the same color as the cover 52; however, consistent with the broader aspects of the present invention and as a matter of design choice, the backing 116 can be semi-transparent or transparent.

The backing material 116 and the pockets 120 and 122 of the journal page are each preferably constructed of substantially lightweight yet durable material including, but not limited to, thermoplastic or polymer materials such as polypropylene, polyethylene, polyester, polystyrene, silicones, polyurethanes, acrylics or combinations/composites thereof. The backing material and pockets can be alternatively or additionally constructed of materials including, but not limited to, laminated or coated papers, cardboard, recycled fibers or other cellulose based or composite materials, provided the pockets themselves are formed of a transparent material. It will be appreciated that the backing and the pockets can be constructed of different types or combinations of materials. As illustrated in FIGS. 7A and 7B, the pockets 120 and 122 are formed on the front surface 118 of the backing 116 by any means known to those skilled in the art. For example, in certain embodiments of the present invention, each pocket 120 and/or 122 can be formed from a single piece of material and adhered, sonic welded or otherwise permanently joined to the front surface 118 of the backing 116 along its sealed edges 124 and 126, respectively, leaving openings 128 and 130, so that items may be inserted therein. Pockets 120 can be sized to receive photographs 30 and/or other mementos. Pockets 122 is sized to receive at least one of the insert cards 74.

Alternatively, in certain embodiments of the present invention, the pockets can be formed by providing a single sheet of transparent material, permanently joining it to the backing 116 to define the sealed edges 124 and 126 of the pockets 120 and 122.

Turning for the moment to FIG. 8, an alternative construction of the journal pages 114, 136, 160, 162, 164, 166 and 168 is illustrated. In particular, rather than including a single pocket 122 that retains a single, larger insert card 74, the journal pages 114, 136, 160, 162, 164, 166 and 168 may instead be constructed of a plurality of pockets 122 which will each retain a smaller insert card 74. The transparent pockets 122 will be formed on the backing 116 by sonic welding or by any means known to those skilled in the art, as described herein.

Figures 1, 2, 3:
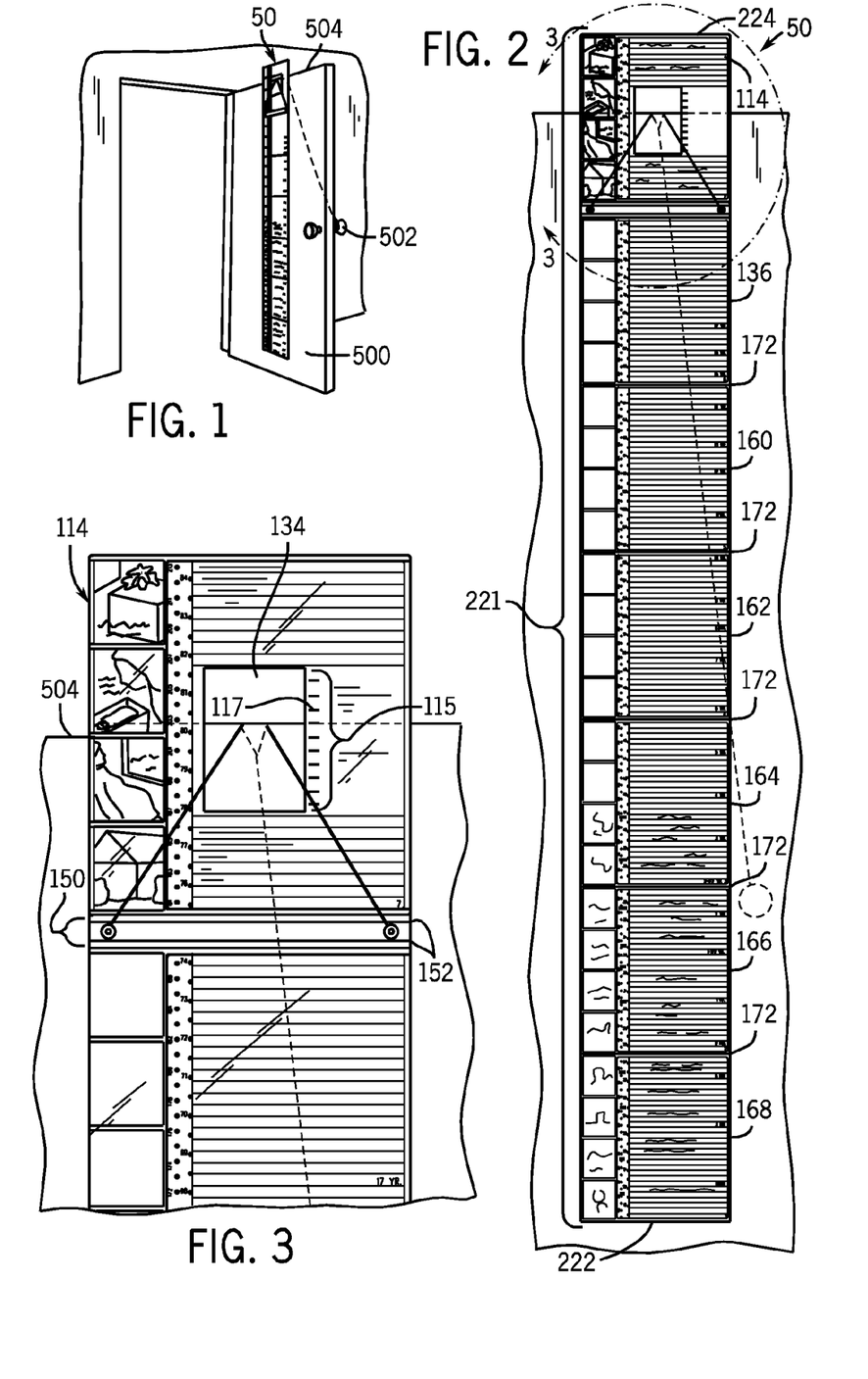
FIG. 1 is a perspective view of a first embodiment of a height recording album of the present invention, including an integral mounting device.
FIG. 2 is a front plan view of the height recording album illustrated in FIG. 1.
FIG. 3 is a partial front view of the height recording album illustrated in FIGS. 1 and 2, taken along the line 3-3 in FIG. 2.

As best illustrated in FIG. 3, the first journal page 114 further includes an aperture 134 substantially the same size as the opening 96 in the front cover 78 and will be aligned therewith to provide a viewing window in the album 50 when the journal page 114 is joined with the cover 52. Measuring indicia 115 located adjacent to the aperture 134 is also provided on the front surface 114a of the journal page 114, which will be used to hang the height album 50 from a door 500 at the proper height, depending on the overall height of the door. The measuring indicia 115 corresponds to the height of a conventional interior door, and therefore, includes calibrated graduations 117 keyed to correspond to door heights ranging from about 78 inches to about 85 inches from the floor to the door's top edge, although a smaller or larger range may be used, as a matter of design choice. The measuring indicia 115 is preferably provided in both English and metric units.

The second journal page 136 is substantially the same size as, or slightly smaller than the rear cover 82 so that it can be mated and adhered or otherwise permanently joined to the inside surface 92 of the rear cover 82. The journal page 136 is preferably connected to the journal page 114 by an area 150 provided by hinge or fold lines 152. The area 150 is substantially the same size as, or slightly smaller than, the spine 80 of the cover 52, so that it can be mated and adhered to the inside surface thereof. The hinge or fold lines 152 can be formed by ultrasonic welding, crimping, or by otherwise providing a living hinge so that the journal pages 114 and 136 are repeatably pivotable about such fold lines 152, as will be well known to those skilled in the art.

Likewise, additional interconnected journal pages 160, 162, 164, 166 and 168 are also provided, each being separated by a hinge or fold line 172. It will be appreciated that although seven journal pages are shown in the Figures, a larger number (or a smaller number) of journal pages may be provided, depending on the desired size of the album, application and as a matter of design choice. In addition, it will be appreciated that the number and size of the transparent pockets formed on the front surface of each of the journal pages 114, 136, 160, 162, 164, 166 and 168 is a matter of design choice, and not limited to the configuration shown in the Figures.

Like journal page 114, the journal pages 136, 160, 162, 164, 166 and 168 are constructed of a durable material selected to protect the contents of the album over a number of years, such as an acid-free material. As such, the pages are preferably constructed of substantially lightweight yet durable material including, but not limited to, thermoplastic or polymer materials such as polypropylene, polyethylene, polyester, polystyrene, silicones, polyurethanes, acrylics or combinations/composites thereof. The backing material and pockets can be alternatively or additionally constructed of materials including, but not limited to, laminated or coated papers, cardboard, recycled fibers or other cellulose based or composite materials, provided the pockets themselves are formed of a transparent material. It will be appreciated that the backing and the pockets can be constructed of different types or combinations of materials.

As illustrated in FIGS. 7 and 8, the journal pages 114, 136, 160, 162, 164, 166 and 168 are preferably constructed from a single, continuous piece of material that will form the backing sheet 116 for each of the journal pages 114, 136, 160, 162, 164, 166 and 168, with the hinge or fold lines 172 formed in between each of the journal pages so that the journal pages can be pivoted/folded with respect to each other. The transparent pockets 120 and 122 on the front surface of each of the journal pages 114, 136, 160, 162, 164, 166 and 168 are preferably formed on the front surface of the continuous sheet of material in the manner described above, or in any manner known to those skilled in the art.

As best illustrated in FIG. 5, the journal page 114, the area 150 and journal page 136 are mated to, aligned with and permanently joined to the inside surface of the front cover 78, spine 80 and rear cover 82, respectively, with an adhesive or by other permanent means known to those skilled in the art. The remaining journal pages 160, 162, 164, 166 and 168 may be folded into an accordion-pleated or fan folded stack 110 and placed between the front and rear covers.

Turning again to FIGS. 7 and 8, the album 50 includes insert cards 74 designed to fit into the pockets 122 of the journal pages 114, 136, 160, 162, 164, 166 and 168, respectively. Each insert card 74 has front and back surfaces, indicated generally at 210 and 212, respectively, and side edges 214. The insert cards 74 are constructed of cardstock, heavy paper, cardboard or thermoplastic material, or alternatively, any material that can be written or printed on by conventional methods.

Each insert card 74 is preferably slightly larger than the pockets 122 so that one 213 of the side edges 214 thereof extends outside the pocket to provide a calibrated portion 216 on the front surface 210 of the card 74. The calibrated portion 216 of the insert card includes measuring indicia 218 and space for marking the height of the child or subject. The measuring indicia 218 is preferably provided in both English and metric units. The remaining portion 220 of each of the cards 74 can be provided with lines for writing information about the child at the time their height is measured and is protected by the transparent pocket. The portion 220 can also be preprinted with indicia 219 such as medical, dental and developmental milestones keyed to the growth of the average child for comparison. The back surface 212 of each of the insert cards 74 can also be used to document, scrapbook, journal or retain information about the child.

When the album 50 is assembled, the pockets 122 of each of the journal pages 114, 136 160, 162, 164, 166 and 168 will contain an insert card 74. As such, when the journal pages 114, 136 160, 162, 164, 166 and 168 are unfolded from the stack 110, the calibrated portion 216 of the insert cards 74 are arranged in proper order, providing the height album 50 with an accurate, graduated measuring scale 221, as illustrated in FIG. 2. The scale 221 starts at the bottom edge 222 of the last journal page 168 and extends to the top edge 224 of the first journal page 114.

Figures 6, 13, 14:
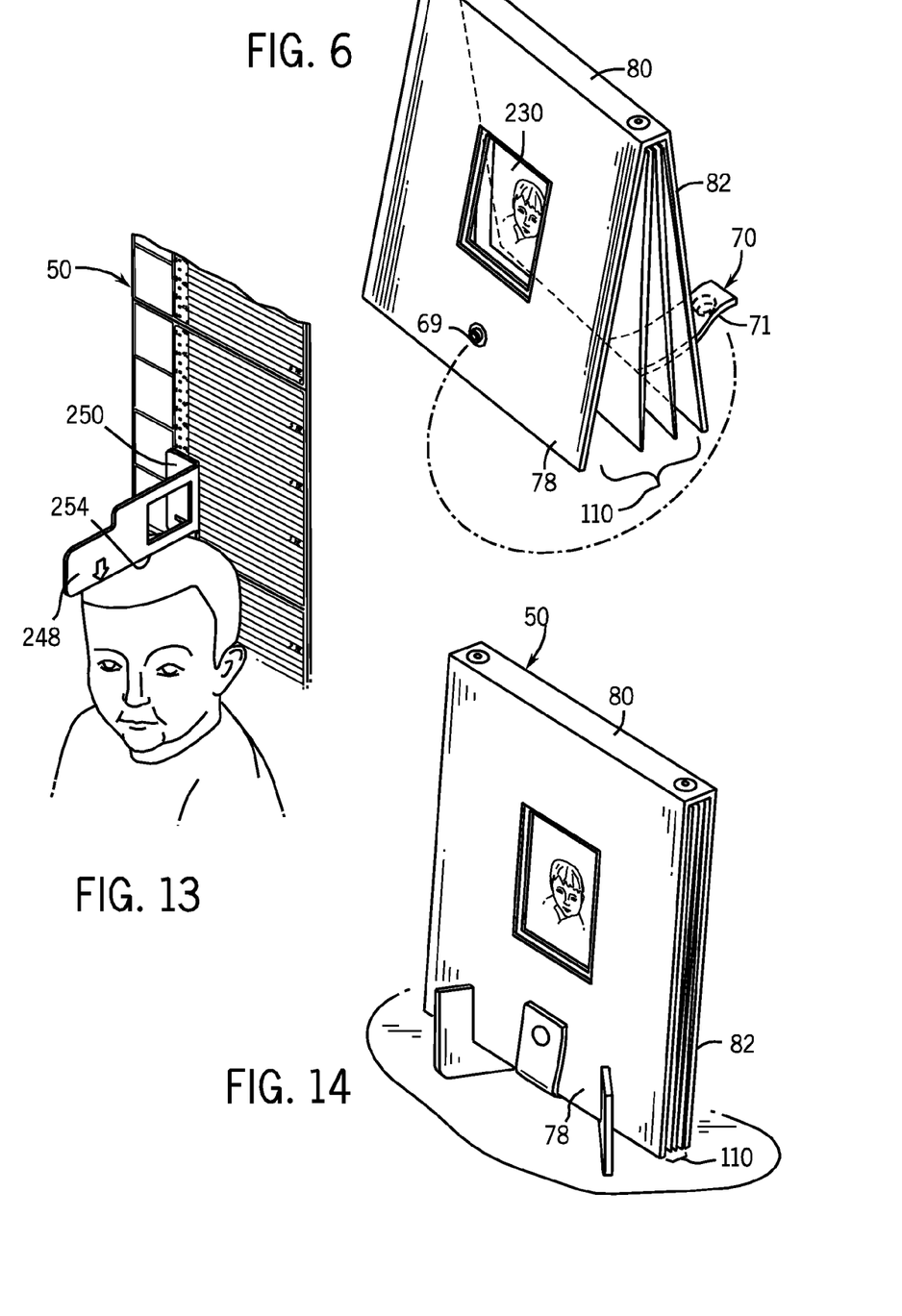
FIG. 6 illustrates the height recording album illustrated in FIGS. 1 through 5, shown in a partially closed position.
FIG. 13 is a partial view of the height recording album illustrated in FIGS. 1 through 11, shown mounted to the door with a subject's height being recorded thereon.
FIG. 14 is a perspective view of the height recording album illustrated in FIGS. 1 through 13, shown in a displayed position on a stand.

As illustrated in FIGS. 4 and 5, an information page 230 is adhered or otherwise joined to the back surface 168b of the journal page 168. As illustrated in FIG. 6, it will be appreciated that when the journal pages are folded into the stack 110, the information page 230 will be oriented to face the inside surface 84 of the front cover 78. The information page 230 is provided with a space 232 for information about the child or subject of the album 50, information about the child's family, etc. The information page 230 further includes an area 234 for providing a photograph of the child or subject of the album 50. The area 234 is positioned on the information page 230 in a manner that will permit the photograph to be seen through the opening 96 in the front cover 78. Additional information or scrap booking pages can be included on the back surfaces of the remaining journal pages 114, 136 160, 162, 164 and 166, as will be well known to those skilled in the art.

Figure 9:
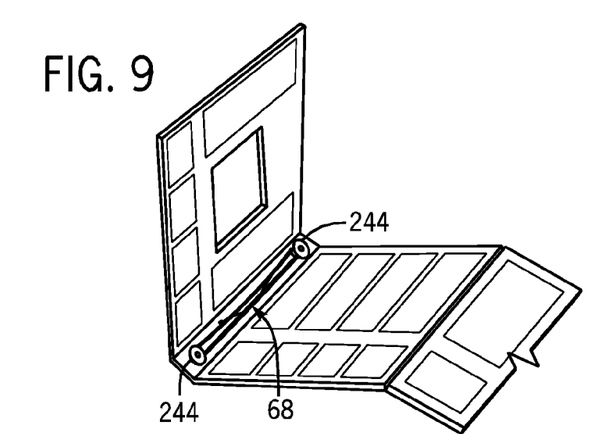
FIG. 9 is a perspective view of the height recording album illustrated in FIGS. 1 through 8, shown with the integral mounting mechanism in a stored position.
Figure 10:
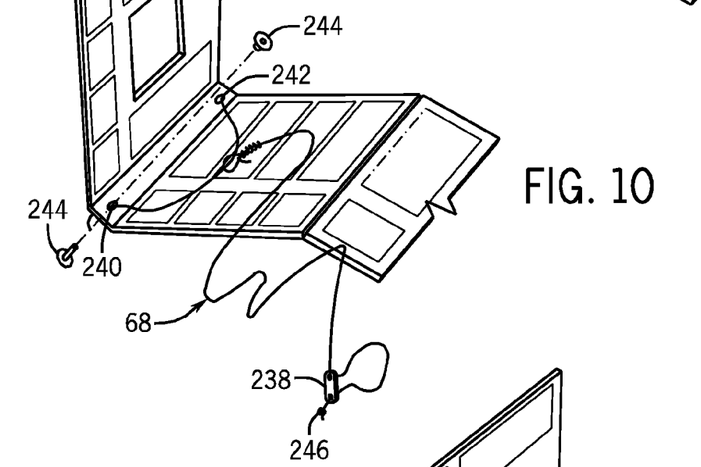
FIG. 10 is a perspective view of the height recording album illustrated in FIGS. 1 through 9, shown with the cord of the integral mounting mechanism unwound from the bobbins.
Figure 11:
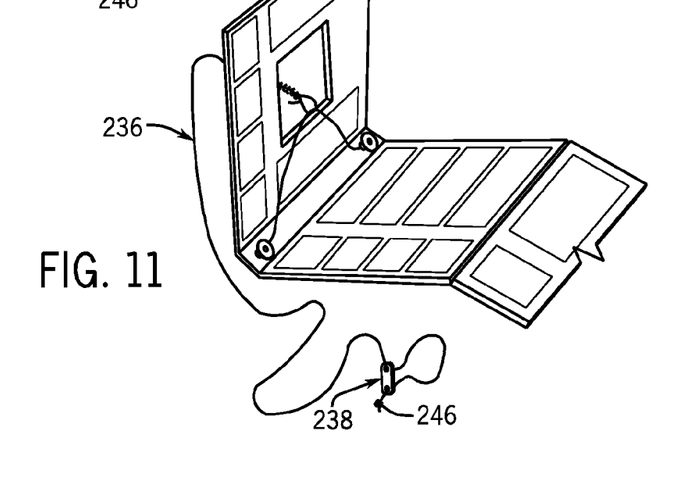
FIG. 11 is a perspective view of the height recording album illustrated in FIGS. 1 through 10, shown with the cord proper in position for mounting the album to a door.
Figure 12A:
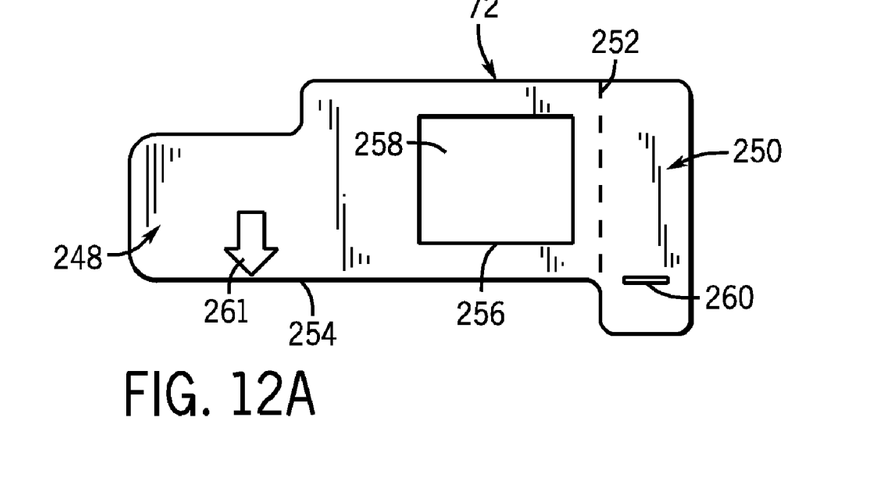
FIG. 12A is a marking card used in the height recording album of the present invention.
Figure 12B:
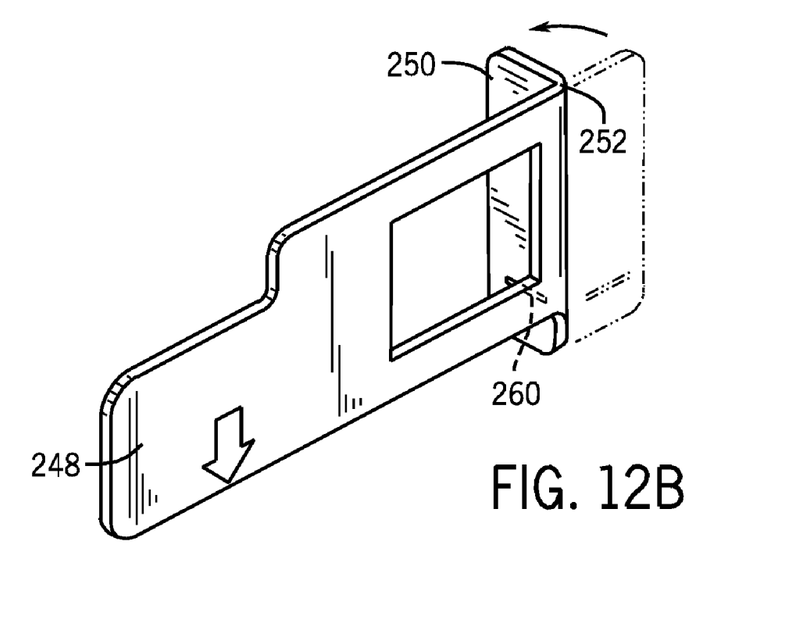
FIG. 12B is a perspective view of the marking card illustrated in FIG. 12A, shown in a folded position.
Figures 15, 16, 17, 18:
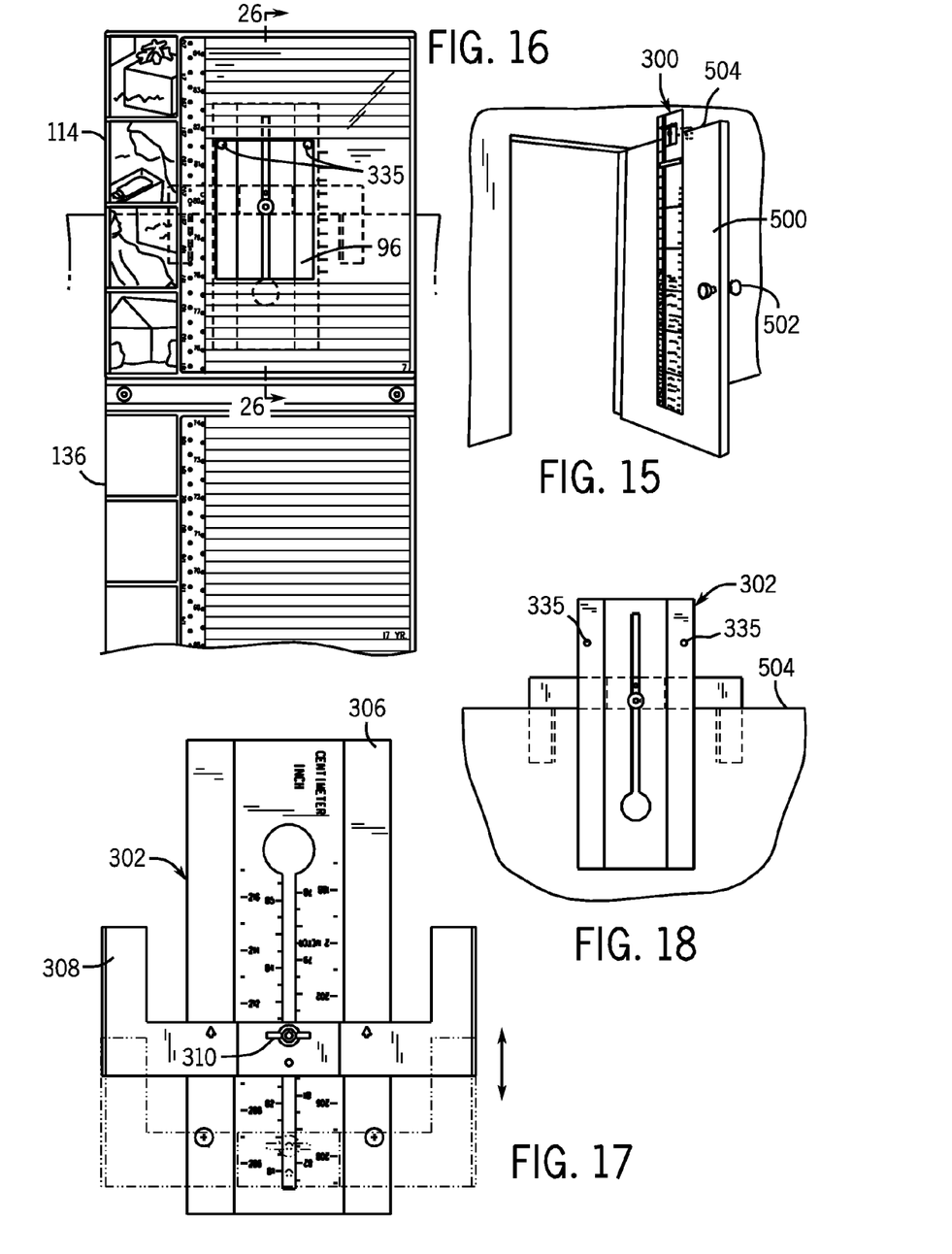
FIG. 15 is a perspective view of a second embodiment of a height recording album of the present invention, including an external mounting device.
FIG. 16 is a partial front view of the height recording album illustrated in FIG. 15, shown mounted to a door.
FIG. 17 is a front view of the external mounting device used with the height recording album shown in FIGS. 15 and 16.
FIG. 18 is a rear view of the external mounting device illustrated in FIG. 17, shown mounted to a door.

Turning next to FIGS. 9 through 11, the mounting mechanism 68 is integrally provided with the album 50 and used to mount the album 50 to the door 500 when height measurements are taken. In certain preferred embodiments of the present invention, the mounting mechanism 68 can include a string or cord 236 and a retainer 238. The cord 236 is configured in substantially a Y-shape, having first ends 240 and 242 that are secured to the inside surface 88 of the spine 80 with rivets, grommets and/or bobbins 244. It will be appreciated that the bobbins 244 are preferably provided after the journal pages are mounted to the cover 50. A second end 246 of the cord 236 is looped to fit over a door knob 502 of the door 500 and includes the retainer 238 for tightening and loosening the loop so that the album 50 can be securely mounted to the door 500. When the album 50 is being displayed, the cord 236 is wrapped around the bobbins 244 for storage, as illustrated in FIG. 9. It will be appreciated that the ends 240 and 244 of the cord 236 can be fastened to the cover 52 by any mechanical or adhesive fastening means known to those skilled in the art.

As illustrated in FIGS. 6 and 14, the closure 70 can be provided to retain the front and rear covers in a closed position when the album 50 is being displayed or otherwise stored. The closure 70 preferably has two portions, a first portion 69 secured to the front cover 78 and a second portion 71 secured to the rear cover 82. For example, the closure 70 can be a snap, clasp, latch, button and/or Velcro. Alternatively, the closure 70 can include a rivet, bobbin or button as the first portion 69, which is secured to the front cover 78; and a string or cord as the second portion 71, which is secured to the rear cover 82, wherein the cord can be wrapped around the bobbin to secure the cover 50 closed. It will be appreciated that certain embodiments of the height album of the present invention can be Turning now to FIGS. 12a and 12b, the height album 50 of the present invention also includes the marking device 72 used to properly mark the subject's height. The marking device 72 has first and second portions 248 and 250 which are connected to and foldable with respect to each other along a hinge or fold line 252. An edge 254 of the first portion 248 is configured to rest on the subject's head when height measurements are taken. A middle section 256 of the first portion 248 of the marking device 72 includes a stencil or cut-out 258 that is substantially the same size as the photograph pockets 120 in the journal pages 114, 136 160, 162, 164, 166 and 168, so that a user may cut a photograph to fit within the pockets. The second portion 250 of the marking device 72 includes an opening or slot 260 which will be used to accurately mark the height of the subject on the journal page. The marking device 72 can further include written indicia 261 with instructions on how to use the marking device. The marking device is preferably constructed of a stiff material such as card stock, laminated papers, thermoplastic, or any material or combination of materials that can be printed using conventional equipment.

To use the height album 50 of the present invention, the closure 70 is unlatched and the cover 52 is opened and the fan folded stack 110 is unfolded so that the journal pages 114, 136 160, 162, 164, 166 and 168 are fully extended. The cord 236 of the mounting mechanism 68 is unwound from the bobbins 244 and it is threaded through the opening 96 in the front cover 78, as illustrated in FIG. 11. As illustrated in FIG. 1, the cord 236 is slipped over the top edge 504 of the door and the retainer 238 on the end 246 of the cord 236 is loosened so that the loop fits over the door knob.

The height of the door from the floor to the top edge of the door is then measured. As illustrated in FIG. 3, using the measuring indicia 115 on the top journal page 114, the top edge 504 of the door 500 is then aligned with the appropriate calibrated graduation 117 for the correct height of the door. The retainer 238 is used to tighten the end 246 of the cord 236 around the door knob 502, fixing the height album 50 at the correct vertical position. Once secured, the calibrated measuring indicia 218 on the insert cards 74 of the height album provides an accurate scale for measuring a child's height.

The marking device 72 is then used to measure the child's height. The marking device 72 is folded along fold line 252 so that the first portion 248 is bent at substantially a right angle with respect to the second portion 250 so that the first portion 248 extends perpendicular to the second portion 250. As such, the second portion will be positioned parallel to and directly against the planar surface of the height album 50 and the first portion 248 extends outwardly therefrom, as illustrated in FIG. 13. The child then stands adjacent to the mounted height album 50. The edge 254 of the first portion 248 is rested on the top of the child's head. The height of the child is marked in the correct location on the extended edge 214 of the insert card 74 using the slot 260 in the second portion 250 of the marking device 72. (The height is preferably marked using a permanent pen or ink). When the child steps away from the height album, their height is indicated on the insert card 74 of the journal page. Once the height measurement is taken, the insert card 74 within the transparent pocket on the journal page can be removed to include information about the child's progress, likes and dislikes, school, etc. on the front and/or back surface thereof. In addition, a photograph, cut to the correct size using the stencil 258 on the marking device 72, can be placed into the transparent pocket next to the marked height measurement—reflecting the child at the age the height is measured.

After the height measurement and journal entry are made, the album is removed from the door by loosening the retainer 238 around the door knob, removing the album 50 from its fixed position and winding the cord 236 around the bobbins 244 for storage. The journal pages 114, 136 160, 162, 164, 166 and 168 are again folded into the fan folded stack 110 with the cover 52 protecting the album's contents. The closure 70 is then fastened.

As illustrated in FIG. 14, the display stand 78 comprises a substantially V-shaped member, that permits the height album 50 to be displayed upright so that a picture showing through the opening 96 in the front cover 78 is displayed and easily viewed, like a picture frame. The display stand 78 can be configured in any way known to those skilled in the art that permits the album 50 to be displayed upright. The display stand 78 is preferably constructed of a substantially rigid material such as reinforced cardboard or thermoplastic, or any material or combination of materials that will support the weight of the album 50 while displayed. Alternatively, the height album 50 may be stored on a shelf with other books.

Turning next to FIGS. 15 through 29, another embodiment of a height album 300 of the present invention is illustrated. Like the height album 50, the height album 300 comprises a cover 52, a plurality of interconnected journal pages, indicated generally at 114, 136, 160, 162, 164, 166 and 168, respectively, for retaining a plurality of insert cards 74, and a closure 70. Also similarly, the height album 300 additionally includes a measuring and marking device 72.

The height album 300 is constructed in the same manner as height album 50, however, height album 50 includes an alternate mounting mechanism and combination display stand 302. As illustrated best in FIGS. 17, 28 and 29, the mounting mechanism 302 is provided separately from the height album 300 and comprises a back plate 306, a hanger bracket 308 and fastening mechanism 310. The mounting mechanism 302 is preferably constructed of a substantially rigid material such as reinforced cardboard or thermoplastic, or any material or combination of materials that will support the weight of the album 300 while mounted or displayed.

Figures 19, 25:
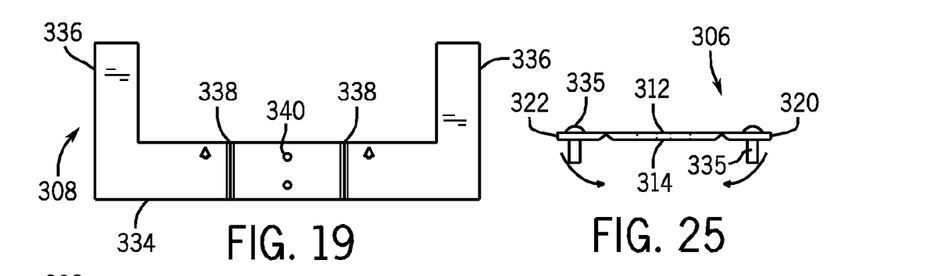
FIG. 19 is a front view of a hanger bracket used with the external mounting device shown in FIGS. 17 and 18.
FIG. 25 is a side view of the calibrated back plate shown in FIG. 24.
Figure 20:
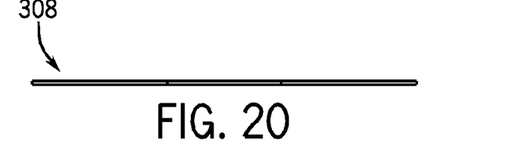
FIG. 20 is a side view of the hanger bracket shown in FIG. 19.
Figure 21:
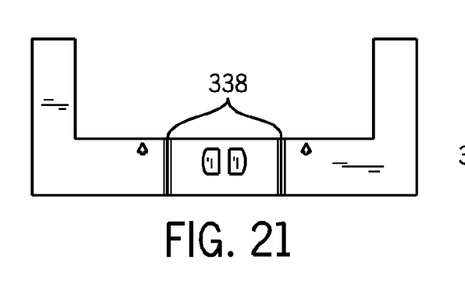
FIG. 21 is a front view of an alternate hanger bracket used with the external mounting device illustrated in FIGS. 17 and 18.
Figure 22:
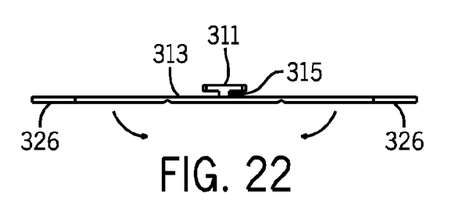
FIG. 22 is a side view of the hanger bracket illustrated in FIG. 21.
Figure 23:
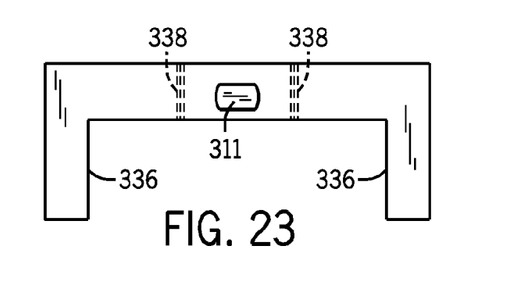
FIG. 23 is a rear view of the hanger bracket illustrated in FIGS. 21 and 22.
Figure 24:
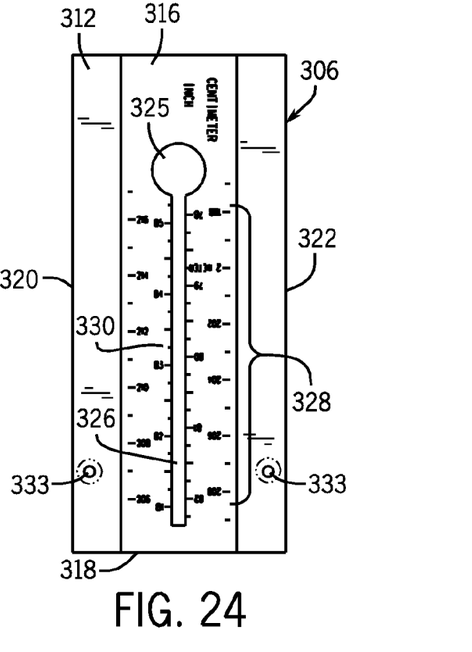
FIG. 24 is a front view a calibrated back plate used with the external mounting device shown in FIGS. 17 and 18.

The back plate 306 is generally rectangular in shape, having front and back surfaces 312 and 314 and edges 316, 318, 320 and 322. Vertical hinge or fold lines 324 permit each of the edges 320 and 322 to pivot or fold so that the back plate 306 can be used as a stand, as described in more detail below. An opening 325 and a vertical slot 326 are provided at approximately the center of the back plate 306. The front surface 312 includes measuring indicia 328 corresponding to the height of a conventional interior door, and therefore, includes calibrated graduations 330 keyed to correspond to door heights ranging from about 78 inches to about 85 inches from the floor to the door's top edge, although a smaller or larger range may be used, as a matter of design choice. The measuring indicia 328 is preferably provided in both English and metric units. The back plate 306 includes laterally spaced apertures 333 sized to accommodate hangers 335, such as pegs, pins or the like to hang the album. Alternatively, extending tabs could be integrally formed on the back plate 306. The hanger bracket 308 is a substantially U-shaped member having a flat bottom portion 334 and laterally spaced legs 336 extending away from the bottom portion 336. Vertical hinge or fold lines 338 permit each of the legs 336 to pivot or fold so that the hanger bracket 308 can be used to mount the album 300 to the top edge 504 of the door 500, or alternatively, when the hanger bracket 308 is used as a stand, as described in more detail below. FIGS. 19 and 20 show a first embodiment of a hanger bracket, wherein apertures 340 are formed so that the bracket can be mounted to the back plate 306; however, another embodiment of a hanger bracket is illustrated in FIGS. 21 through 23, wherein a guide 311 is provided, in addition to the apertures 340 for mounting the bracket to the back plate.

The guide 311 extends perpendicularly outward from a surface 313 of the hanger bracket 308. The guide 311 is sized to fit through the opening 325 in the back plate 306, including a portion 315 designed to slide back and forth within the slot 326 therein. At least one aperture 340 sized to receive the fastening mechanism 310 is provided in approximately the center of the bottom portion 334 of the bracket 308. The aperture 340 is positioned to align with the slot 326 of the back plate 306 so that the fastening mechanism may removably secure the back plate 306 and bracket 308 together. The fastening mechanism 310 can be a screw/wing nut, snaps or any device capable of securing the back plate 306 and bracket 308 together and also bearing the weight of the album 300.

To use the height album 300 of the present invention, the closure 70 is unlatched and the cover 52 is opened and the fan folded stack 110 is unfolded so that the journal pages 114, 136 160, 162, 164, 166 and 168 are fully extended. The height of the door from the floor to the top edge of the door is then measured.

The hanger bracket 308 is positioned in its inverted position (upside down U position) with its legs 336 pivoted substantially ninety degrees away from the bottom portion 334 thereof, providing the hanger bracket with a hook-like feature. The bracket is moved so that a bottom edge 342 of the bottom portion 334 is aligned with the appropriate calibrated graduation 330 for the correct height of the door. The fastening mechanism 310 is then threaded through the aperture 340 in the bracket 308 and the slot 326 in the back plate 306, securing them together. The mounting mechanism 302 is then positioned so that the hanger bracket 308 rests on the top edge of the door.

In this position, the tabs 332 project forward a distance sufficient to permit the album 300 to be hung therefrom. As such, the album 300 is then mounted to the top edge of the door by hanging it on the back plate tabs 332 using the opening 96 in the front cover 78. Once secured, the calibrated measuring indicia 218 on the insert cards 74 of the height album 300 provides an accurate scale for measuring a child's height.

The marking device 72 is then used to measure the child's height. The marking device 72 is folded along fold line 252 so that the first portion 248 is bent at substantially a right angle with respect to the second portion 250 so that the first portion 248 extends perpendicular to the second portion 250. As such, the second portion will be positioned parallel to and directly against the planar surface of the height album 300 and the first portion 248 extends outwardly therefrom. The child then stands adjacent to the mounted height album 300. The edge 254 of the first portion 248 is rested on the top of the child's head. The height of the child is marked in the correct location on the extended edge 214 of the insert card 74 using the slot 260 in the second portion 250 of the marking device 72. (The height is preferably marked using a permanent pen or ink). When the child steps away from the height album, their height is indicated on the insert card 74 of the journal page.

Once the height measurement is taken, the insert card 74 within the transparent pocket on the journal page can be removed to include information about the child's progress, likes and dislikes, school, etc. on the front and/or back surface thereof. In addition, a photograph, cut to the correct size using the stencil 258 on the marking device 72, can be placed into the transparent pocket next to the marked height measurement—reflecting the child at the age the height is measured.

After the height measurement and journal entry are made, the album 300 is pulled away from the tabs 332 of the mounting mechanism 302. The journal pages 114, 136 160, 162, 164, 166 and 168 are again folded into the fan folded stack 110 with the cover 52 protecting the album's contents. The closure 70 is then fastened.

Figures 26, 27, 28, 29:
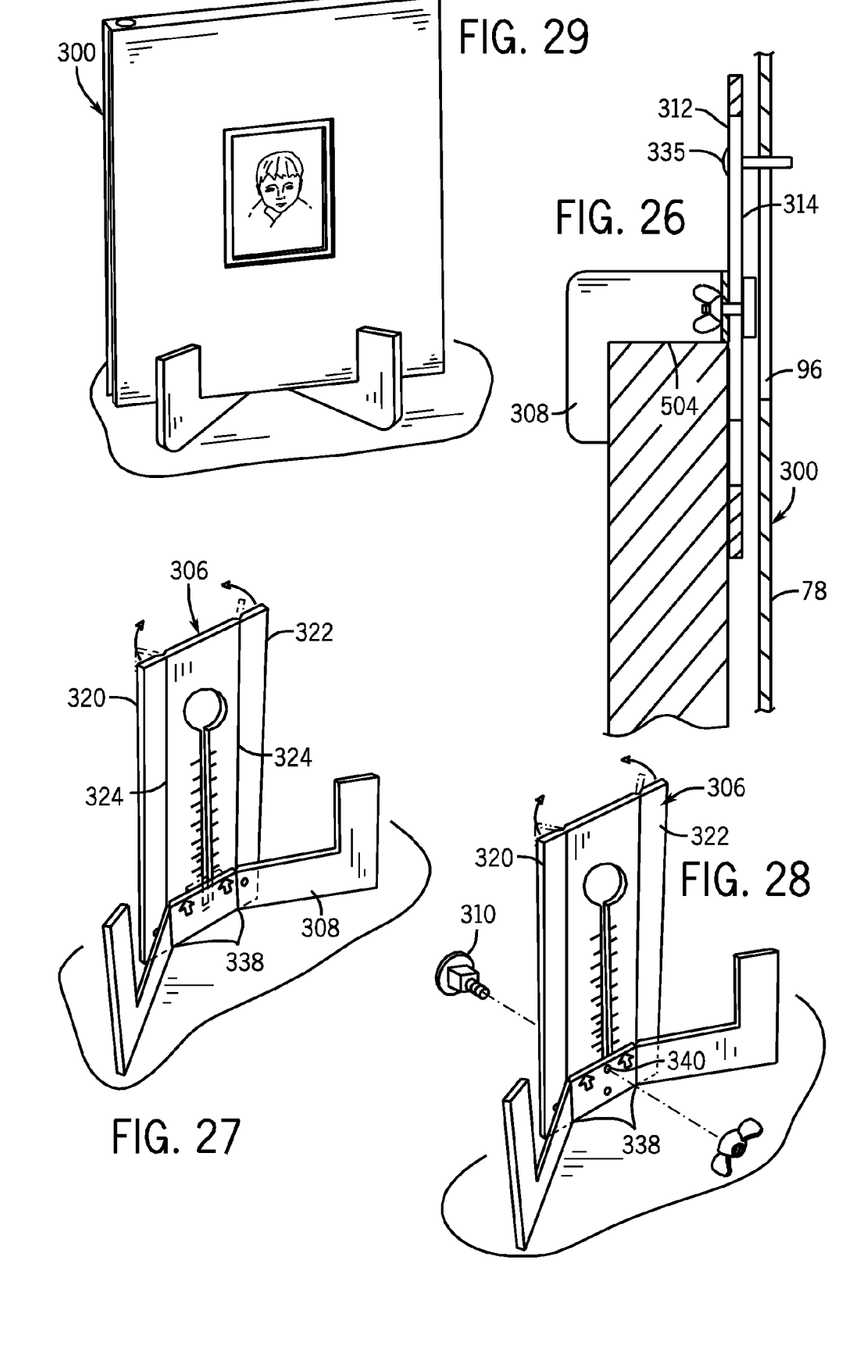
FIG. 26 is a partial side view of the height recording album of the present invention, shown mounted to the door with the external mounting device of FIGS. 15 through 25, taken along the line 26-26 in FIG. 16.
FIG. 27 is a perspective view of the external mounting device of FIGS. 15 through 26, shown partially assembled into a stand.
FIG. 28 is a perspective view of the external mounting device of FIGS. 15 through 27, shown partially assembled.
FIG. 29 is a perspective view of the height recording album illustrated in FIGS. 15 through 28, shown in a displayed position on a stand.

The mounting mechanism 302 is then converted into a display stand 350 as illustrated in FIGS. 27 through 29. The fastening mechanism 310 is loosened or removed so that the hanger bracket 308 can be positioned in an upright position (U position) and then the fastening mechanism 310 is retightened. Legs 336 of the bracket 308 are pivoted substantially ninety degrees away from the bottom portion 334 thereof. The edges 320 and 322 of the back plate 306 are folded along fold lines 324 to provide stability to the back plate 306. The album 300 can then be displayed in the stand 350.

Consistent with the broader aspects of the present invention, one skilled in the art will appreciate that the height albums 50 and 300 of the present invention, can be mounted to a wall, rather than to a door, and height measurements taken as described above.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A height recording album for documenting a subject's height measurements, the album comprising:
    a front cover having, a spine and a rear cover, the front cover including an opening formed therein and each of the front cover, spine and rear cover having an inside surface and an outside surface;
    a plurality of interconnected journal pages, each of the interconnected journal pages having at least one transparent pocket formed thereon, a first journal page of the plurality of interconnected journal pages having an aperture including a bottom edge and a top edge, the aperture being substantially the same size as the aperture in the front cover, the first journal page further including vertically aligned door height indicia ranging from the bottom edge to the top edge of the aperture, wherein the first journal page is adhered to the inside surface of the front cover and a second journal page of the plurality of interconnected journal pages is adhered to the inside surface of the rear cover, wherein the plurality of interconnected journal pages are configurable between a fully extended position and a stored, fan folded position;
    at least one insert card removably positioned inside the at least one transparent pocket on each of the journal pages;
    measuring indicia provided on the at least one insert card on each of the journal pages, wherein the measuring indicia provides a vertically calibrated scale extending from substantially a bottom edge of a last journal page of the plurality of interconnected journal pages to substantially a top edge of the first journal page of the plurality of interconnected journal pages; and
    a mounting mechanism secured to the inside surface of the spine.

2. The height recording album of claim 1, wherein the front cover, spine and rear cover are constructed of a single piece of material.

3. The height recording album of claim 1, wherein the front cover, spine and rear cover are constructed of a substantially rigid material selected from thermoplastic, cardboard, paper and combinations thereof.

4. The height recording album of claim 1, wherein each of the plurality of interconnected journal pages includes an opaque backing material, wherein the at least one transparent pocket is secured thereto.

5. The height recording album of claim 4, wherein the opaque backing material is a thermoplastic material and wherein the at least one transparent pocket is a thermoplastic material sonic welded thereto.

6. The height recording album of claim 4, wherein each of the plurality of interconnected journal pages is constructed of a single piece of backing material.

7. The height recording album of claim 1, wherein each of the plurality of interconnected journal pages further comprises a vertically aligned set of transparent pockets positioned adjacent to the measuring indicia on each of the at least one insert cards.

8. The height recording album of claim 1, wherein the at least one insert card includes a first portion that extends outside the at least one pocket, the portion including the measuring indicia printed thereon.

9. The height recording album of claim 1, wherein the at least one insert card includes a second portion having child milestone indicia printed thereon.

10. The height recording album of claim 1, wherein the measuring indicia is provided in both English and metric units.

11. The height recording album of claim 1, wherein the mounting mechanism comprises a cord configured in a Y-formation, the cord have first ends secured in a laterally spaced orientation to the inside surface of the spine and a second end including an adjustable loop configured to removably secure to a door knob.

12. The height recording album of claim 11, wherein the mounting mechanism is mounted to the spine with rivets or bobbins, and wherein the mounting mechanism is has a stored position in which the cord to wrapped around the bobbins on the inside surface of the spine.

13. The height recording album of claim 1, further comprising a closure secured to at least one of the front cover, spine and rear cover for holding the front cover closed with respect to the rear cover.

14. A height recording album for documenting a subject's height measurements, the album comprising:
    a cover including a front cover, a spine and a rear cover, the front cover including an aperture formed therein, each of the front cover, spine and rear cover having an inside surface and an outside surface;
    a plurality of interconnected journal pages, each page defined by a top edge and a bottom edge, wherein a first journal page of the plurality of interconnected journal pages includes an opening formed therein and is adhered to the inside surface of the front cover and wherein a second journal page of the plurality of interconnected journal pages is adhered to the inside surface of the rear cover, wherein the plurality of interconnected journal pages is configurable between a fully extended, operational position and a fan folded, stored position;

door height indicia provided adjacent the opening in the first page;

calibrated measuring indicia provided on the plurality of interconnected journal pages, the calibrated indicia beginning at substantially the bottom edge of a last journal page of the plurality of interconnected journal pages and ending at substantially the top edge of the first journal page of the plurality of interconnected journal pages; and a mounting mechanism secured to the inside surface of the spine.

15. The height recording album of claim 14, wherein each of the plurality of interconnected journal pages comprises a backing material having at least one transparent pocket secured thereto.

16. The height recording album of claim 15, further comprising an insert card removably positioned in the at least one pocket.

17. The height recording album of claim 16, wherein the insert card includes a first portion that extends outside the at least one pocket, the first portion including the calibrated measuring indicia printed thereon.

18. The height recording album of claim 17, wherein the at least one insert card includes a second portion having child milestone indicia printed thereon.

19. The height recording album of claim 15, wherein each of the plurality of interconnected journal pages is constructed of a single piece of backing material.

20. The height recording album of claim 14, wherein the mounting mechanism comprises a cord configured in a Y-formation, the cord have first ends secured in a laterally spaced orientation to the inside surface of the spine and a second end including an adjustable loop configured to removably secure to a door knob.

21. A height recording album securable to a door and configurable between a stored position and a mounted, measuring position, the height recording album comprising:

a cover including a front cover, a spine and a rear cover, the front cover including an aperture formed therein, each of the front cover, spine and rear cover having an inside surface and an outside surface;

a plurality of interconnected journal pages, each page defined by a top edge and a bottom edge, wherein a first journal page of the plurality of interconnected journal pages includes an opening formed therein and is adhered to the inside surface of the front cover and wherein a second journal page of the plurality of interconnected journal pages is adhered to the inside surface of the rear cover, wherein the plurality of interconnected journal pages is configurable between a fully extended, operational position and a fan folded, stored position;

calibrated measuring indicia provided on the plurality of interconnected journal pages, the calibrated indicia beginning at substantially the bottom edge of a last journal page of the plurality of interconnected journal pages and ending at substantially the top edge of the first journal page of the plurality of interconnected journal page; and a removable mounting mechanism, the mounting mechanism including a bracket configured to fit over a top edge of the door and a back plate removably secured to the bracket, the back plate including door height indicia on a first surface thereof and laterally spaced tabs extending away from a second surface thereof, wherein the tabs are configured to engage the aperture in the front cover of the album.

* * * * *